(12) United States Patent
Gupta

(10) Patent No.: US 9,567,722 B2
(45) Date of Patent: *Feb. 14, 2017

(54) TEST DEVICE FOR DETERMINING THREE-DIMENSIONAL CONSOLIDATION PROPERTIES OF SOILS

(71) Applicant: Ramesh Chandra Gupta, Ashburn, VA (US)

(72) Inventor: Ramesh Chandra Gupta, Ashburn, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/729,157

(22) Filed: Jun. 3, 2015

(65) Prior Publication Data

US 2015/0267370 A1 Sep. 24, 2015

(51) Int. Cl.
| | | |
|---|---|---|
| *E02D 1/02* | (2006.01) | |
| *G01N 33/24* | (2006.01) | |
| *G01N 3/08* | (2006.01) | |

(52) U.S. Cl.
CPC .............. *E02D 1/025* (2013.01); *E02D 1/027* (2013.01); *G01N 33/24* (2013.01); *G01N 3/08* (2013.01)

(58) Field of Classification Search
CPC ........ E21B 49/006; E02D 1/022; E02D 1/025; E02D 1/027; G01N 3/08; G01N 3/00; G01N 3/10; G01N 33/24
USPC ......... 73/784, 785, 788, 789, 790, 798, 803, 73/760
See application file for complete search history.

(56) References Cited

U.S. PATENT DOCUMENTS

| | | | | |
|---|---|---|---|---|
| 4,122,704 A | * | 10/1978 | Lutenegger | G01N 3/10 73/822 |
| 4,542,655 A | * | 9/1985 | Park | G01B 5/30 73/152.59 |
| 5,025,668 A | * | 6/1991 | Sarda | G01N 3/10 73/795 |
| 5,226,310 A | * | 7/1993 | Steiger | E21B 49/006 73/38 |

(Continued)

FOREIGN PATENT DOCUMENTS

| | | | |
|---|---|---|---|
| JP | 52030488 A | * | 3/1977 |
| SU | 1425516 | * | 9/1988 |

OTHER PUBLICATIONS

ASTM Standards, Standard Test Method for Determining One-Dimensional Consolidation Properties of Soils,2011,ASTM D2435/D2435 M-11,American Society of Materials,Philadelphia,US.

(Continued)

*Primary Examiner* — Lisa Caputo
*Assistant Examiner* — Nathaniel T Woodward

(57) ABSTRACT

A test device has been invented for determining three-dimensional consolidation properties of soils, using a flexible ring permitting displacements and dissipation of the excess pore pressures in both horizontal and vertical directions, and affording determination of coefficients of consolidation in the horizontal and vertical directions, and the modulus of elasticity. The flexible ring consists of a filter fabric around the soil specimen, a rubber membrane around the filter, circular shaped segmented stainless steel plates around the membrane and rubber bands around the plates. Both the incremental loading or triaxial type loading systems can be used with this device. A calibration device for calibration of the flexible ring is used to determine the modulus of elasticity of elastic elements, required for cal- (Continued)

culating lateral resistance provided by the flexible ring during the test.

2 Claims, 14 Drawing Sheets

(56) References Cited

U.S. PATENT DOCUMENTS

| | | | | |
|---|---|---|---|---|
| 5,275,063 A * | 1/1994 | Steiger | G01N 33/241 | 73/865.6 |
| 5,435,187 A * | 7/1995 | Ewy | G01N 3/10 | 73/38 |
| 6,595,068 B2 * | 7/2003 | Brovold | G01N 3/10 | 73/803 |
| 6,655,220 B1 * | 12/2003 | Reiffsteck | E02D 1/04 | 73/152.59 |
| 7,520,177 B2 * | 4/2009 | Secq | G01B 5/30 | 73/795 |
| 7,536,921 B1 * | 5/2009 | Chu | G01N 3/10 | 73/760 |
| 7,694,581 B2 * | 4/2010 | Secq | G01B 5/30 | 73/760 |
| 2005/0039540 A1 * | 2/2005 | Crockford | G01L 5/0004 | 73/784 |
| 2010/0089124 A1 * | 4/2010 | Katti | E02D 1/027 | 73/38 |

OTHER PUBLICATIONS

ASTM Standards, Standard Test Method for Consolidated Undrained Triaxial Compression Test for Cohesive Soils,2011,ASTM: D4767-1,American Society of Materials, Philadelphia,US.

AASHTO, Standard Method of Test for One-Dimensional Consolidation Properties of Soils, 2012, American Association of State Highway and Transportation Officials, Washington,US.

Fang, H, Foundation Engineering Handbook, 1990, 2nd Edition, Van Nostrand Reinhold, New York.

HRB, Estimating Consolidation Settlements of Shallow Foundations on Overconsolidated Clay,1973, Application Bulletin by Committee A2L02, Properties of Soli and Rock.

Perloff, W. H., and Baron, W. (1976), Soil Mechanics, John Wiley and Sons, New York.

Skempton, A. W., and Bjerrum, L. (1957), A Contribution to the Settlement Analyses of Foundations on Clay, Geotechnique 7, No. 3.

Terzaghy, K, Peck, B. P., Mesri, G. (1996), Soil Mechanics in Engineering Practice, Wiley-Interscience, New York.

Winterkorn H. F., and Fang, H. (1975), Foundation Engineering Handbook, Van Nostrand Reinhold Company, New York.

* cited by examiner

TEST DEVICE FOR DETERMINING THREE-DIMENSIONAL CONSOLIDATION PROPERTIES OF SOILS

CROSS REFERENCE TO RELATED APPLICATIONS (IF ANY)

This specification is complete in itself.

STATEMENT OF FEDERALLY SPONSORED RESEARCH/DEVELOPMENT (IF ANY)

This invention is not sponsored or supported by federally sponsored research or development. This invention has been developed by me, Dr. Ramesh Chandra Gupta, Ph. D., P.E, President and Sole Owner of SAR6 INC., solely at my own cost and time.

The names of the parties to a joint research agreement if the claimed invention was made as a result of activities within the scope of a joint research agreement.

There is no joint research agreement with anyone. As stated earlier, this research/invention was conceived and completed solely by me (Dr. Ramesh C. Gupta, the inventor). It is my individual research work for this invention.

Reference to a "Sequence Listing," a table, or computer program listing appendix submitted on a compacted disc and incorporation by reference of the material on compact disc. The total number of compact disc including duplicates and the files on each compact disc shall be specified.

List of figures and tables with figure with figure and table captions has been included in Item 8. The whole package is submitted in PDF format attached to the email. A compact disc containing the whole package can be submitted on demand from Patent Office.

BACKGROUND OF THE INVENTION

Standard test methods for determining one-dimensional consolidation properties of soils using incremental loading in accordance with ASTM D2435, or AASHTO . . . , and of those of other international and organizations, do not accurately predict the consolidation properties such as values of vertical settlement, coefficients of consolidation in horizontal ($c_h$) and vertical directions ($c_v$), and modulus of elasticity (E); because fixed ring used in these tests do not allow horizontal displacement and dissipation of excess pore-water pressures in horizontal direction, whereas, in field, under application of a vertical load, both horizontal and vertical settlements occur along with dissipation of excess pore-water pressures in both vertical and horizontal directions. To overcome this more than 100 year old problem, the inventor (Dr. Ramesh Chandra Gupta, Ph. D., P.E.) has invented a test device for determining three-dimensional consolidation properties of soils, using a flexible ring which permits development of horizontal and vertical displacements, and dissipation of excess pore-water pressures in both horizontal and vertical directions, along with increased lateral resistance as takes place in field at any depth in a soil deposit when a vertical load is applied at the surface, The flexible ring consists of filter fabric around the soil specimen, rubber membrane around the filter fabric, circular segmental metal plates around the membrane and elastomeric rubber bands or spring loaded jacket around the segmental plates to allow horizontal and vertical displacements, dissipation of excess pore-water pressures in horizontal and vertical directions, and increased lateral resistance with each increment of vertical load. Therefore, new test device, which simulates field condition, shall allow accurate determination of three-dimensional consolidation properties of soils (such as vertical and horizontal settlements, coefficients of consolidation ($c_v$ and $c_h$) in horizontal and vertical directions and modulus of elasticity.

For this new test device, conventional incremental consolidation frame shall be used for applying vertical load increments, each to be maintained for 24 hours for allowing dissipation of excess pore-water pressures. Triaxial type chamber system shall also be used after suitably modifying to adapt new 3-D consolidation device. With triaxial type chamber system, some modifications shall also be done to adapt to Incremental consolidation frame in place of triaxial loading system to compare which is more suitable of these two loading systems for three-dimensional consolidation tests.

BRIEF SUMMARY OF THE INVENTION

This invention introduces a test device for determining three dimensional consolidation properties of soils using a flexible ring. The flexible ring consists of filter fabric around the soil specimen, rubber membrane around the filter fabric, circular segmental metal plates around the membrane and elastomeric rubber bands or spring loaded jacket around the segmental plates to allow horizontal and vertical displacements, dissipation of excess pore-water pressures in horizontal and vertical directions, and increased lateral resistance with each increment of vertical load. Therefore, new test device which simulates field condition, shall allow accurate determination of three-dimensional consolidation properties of soils (such as vertical and horizontal settlements, coefficients of consolidation ($c_v$ and $c_h$) in horizontal and vertical directions and modulus of elasticity.

This is new invention of a test device to determine three-dimensional consolidation properties of soils. So far only one-dimensional consolidation properties have been determined using ASTM D2435 and AASHTO 216. One-dimensional consolidation devices do not simulate field conditions and therefore do not provide accurate values of consolidation properties.

DETAILED DESCRIPTION OF THE INVENTION

Detailed description of the invention has been explained below in Sections (a) though (g).

(a) Standard Test Methods and Their Limitations

Figure 1:
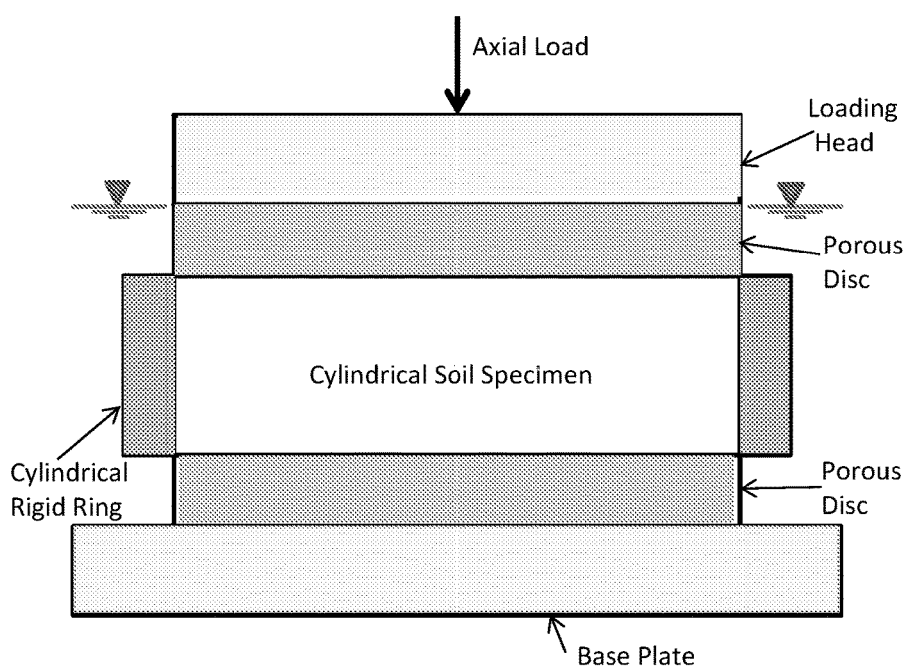
FIG. 1 describes the test device for determining one-dimensional consolidation properties of soils.

The standard test method for one-dimensional consolidation properties of soils using incremental loading is described in ASTM Designation: D2435/D2435M-11 and in AASHTO 216. International and national organizations of several countries have their own standards for this test. The test apparatus consists of a rigid ring as shown in FIG. 1. The soil specimen is pushed in the ring to perform the test.

When foundation loads are transmitted to cohesive subsoils, there is a tendency for a volumetric strain which in the case of saturated material is manifested in an increase in pore water pressure. With sufficient elapsed time, water flows out of the soil pores, permitting excess pore water pressure to dissipate. The analysis of the volumetric strains which result, and the vertical settlements accompanying them, is simplified if we assume that such strains occur only in vertical direction. Such an assumption may not be unreasonable when the geometric and boundary conditions in the field are such that vertical strains dominate. For example, when dimensions of the loaded area are large relative to the thickness of the compressible stratum and/or when the compressible material lies between two stiffer soils whose presence tends to reduce the magnitude of horizontal strains, an approximately one-dimensional compression of the soil will occur (Perloff and Baron, 1976).

However, generally, the above mentioned example rarely occurs. In most cases, three-dimensional consolidation and settlements occur. Therefore volumetric strains in soils significantly depend on displacements both in vertical and horizontal or radial directions. In those cases in which the thickness of compressible strata is large related to the loaded area, the three dimensional nature of the problem shall influence the magnitude and rate of settlement. Although numerical analysis methods offer the prospect of rational consideration of three-dimensional compression effects, they have not proven useful in practice (Winterkorn and Fang, 1990). In view of this, semi-empirical approaches have been used for estimating three-dimensional consolidation properties. The most commonly applied method was developed by Skempton and Bjerrum (1957), using two assumptions: (1) even though the induced excess pore water results from three-dimensional effects, the settlements are assumed as one-dimensional, (2) to account for three-dimensional consolidation, the vertical settlement at the centerline is predicted as equal to product of one-dimensional consolidation settlement times a factor $\lambda$. The value of $\lambda$ is estimated using a chart, which has been plotted based on overconsolidation ratio and ratio of the width of foundation with thickness of consolidating stratum (HRB, 1973).

The coefficients of permeability and consolidation in horizontal direction has been found to be much greater than the coefficients of permeability and consolidation in vertical direction of the same soil deposits or stratum (Terzaghi et al. 1996). Depending on the anisotropy of the soil deposits or presence of very thin sand/silt layers in the soil deposits, the coefficients of permeability in horizontal direction could be even 10 times greater than the coefficients of permeability and consolidation in vertical direction. In such cases, the method of Skempton and Bjerrum (1957) using $\lambda$ factor cannot be applied.

In view of the above, it is very important to develop a test which can determine the three-dimensional consolidation properties of soil deposits. To solve this more than 100 year old problem, the inventor has invented a three-dimensional consolidation test device which permits the dissipation of excess pore water pressure both in vertical and horizontal (radial directions) directions along with settlements occurring both in vertical and horizontal (radial) directions.

(b) Three-Dimensional Consolidation Test Device

Three-dimensional consolidation device consists of a flexible ring instead of a rigid ring as used for one-dimensional consolidation test. The flexible ring consists of about 10 stainless steel segment plates, circular arch in shape for 2.87" (72.9 mm) diameter specimen as shown in FIG. 2 through FIG. 5. The thickness of plates may vary between ⅛" and ⅜" (3.2 mm and 9.53 mm) in thickness. Thicker segmental will not bend under the force exerted by elastomeric rubber bands and in this respect may have some advantage over thinner plates. When vertical load is applied on soil specimen, vertical and horizontal displacement shall occur in the soil specimen, the elastomeric rubber bands around the flexible ring shall expand to allow the horizontal displacement to occur.

Figure 2:
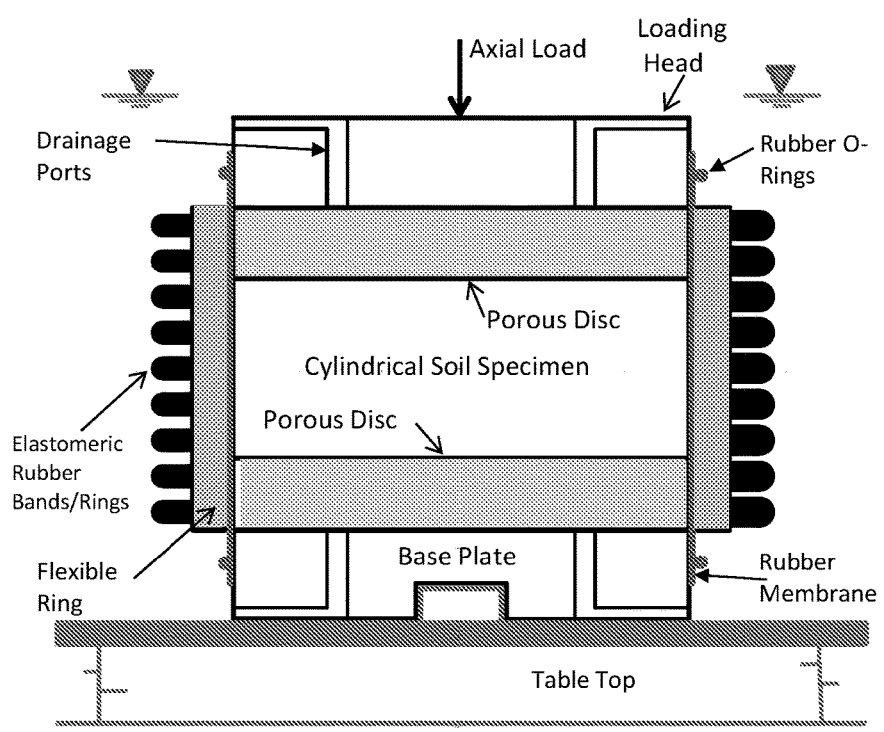
FIG. 2 shows three-dimensional test device permitting both horizontal and lateral displacement but allowing dissipation of excess pore-water pressures only vertical direction.

FIG. 2 shows the schematic detail of a test when dissipation of excess pore water pressures can take place only in vertical direction, but unlike one-dimensional consolidation test, displacements both in vertical and horizontal (radial) directions can take place simultaneously when the vertical load is applied. This test shall permit the determination of coefficient of consolidation in vertical direction.

Figure 3:
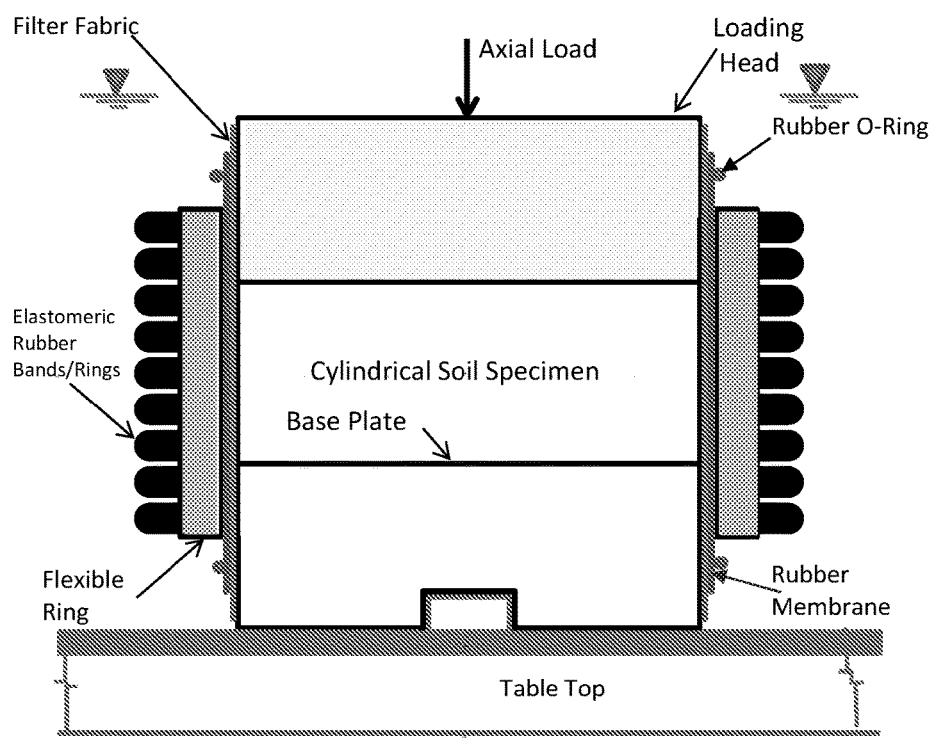
FIG. 3 shows three-dimensional test device permitting both horizontal and lateral displacement but allowing dissipation of excess pore-water pressures only horizontal (radial) direction.

FIG. 3 shows the schematic detail of a test when dissipation of excess pore water pressures can take place only in horizontal (radial directions) direction, but unlike one-dimensional consolidation test, displacements both in vertical and horizontal (radial) directions can take place simultaneously when the vertical load is applied. This test shall permit the determination of coefficient of consolidation in horizontal direction. For this test, a filter fabric is wrapped around the soil specimen. A thick rubber membrane is then installed around the filter fabric. It may be noted that the filter fabric extends both below and top of the rubber membrane to allow dissipation of pore water pressures. Porous discs are not required for this test as dissipation of pore-water pressures in vertical direction are not allowed in this test.

Figure 4:
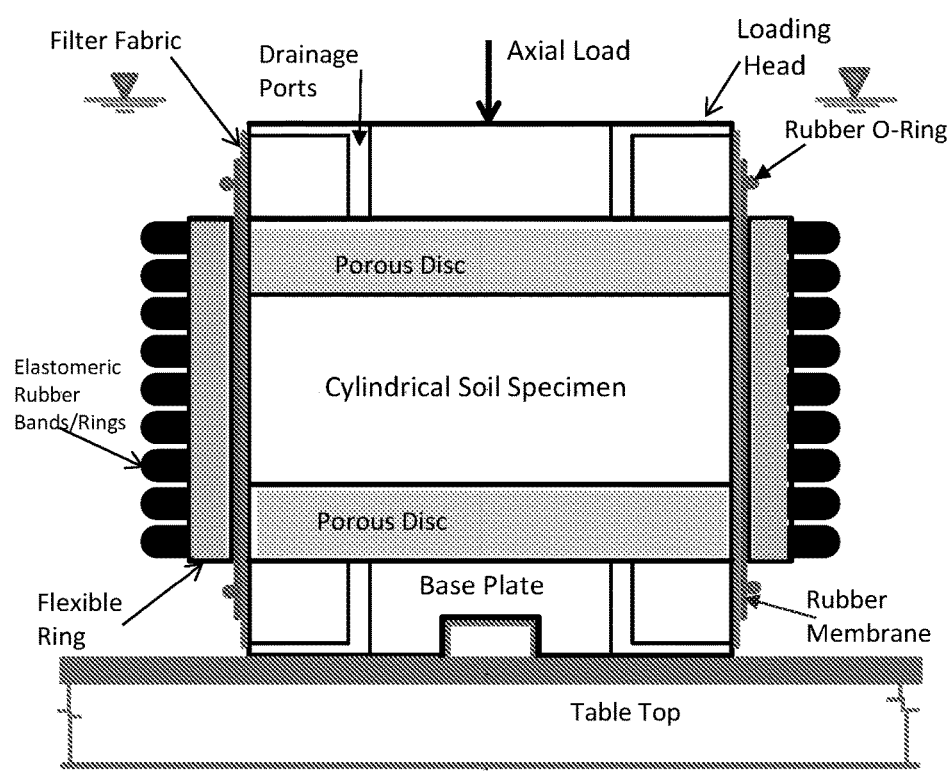
FIG. 4 shows three-dimensional consolidation device permitting both horizontal and lateral displacement and also allowing dissipation of excess pore-water pressures both horizontal and vertical directions.

FIG. 4 shows the schematic detail of a test when dissipation of excess pore water pressures can take place both in vertical and horizontal (radial) directions, but unlike one-dimensional consolidation test, displacements both in vertical and horizontal (radial) directions can take place simultaneously when the vertical load is applied. This test shall permit the determination of three-dimensional coefficient of consolidation. In this test, three-dimensional consolidation shall take place exactly the same way as will take place in insitu conditions in the field. As shown in FIG. 4, porous discs are used to allow dissipation of pore-water pressures in vertical direction and filter fabric around soil specimen is used to allow dissipation of excess pore-water pressures in horizontal (radial) direction.

If the field conditions are such that the drainage boundary is only at the top of the soil deposit and not below it, then the porous disc at the bottom shall be replaced by metal plate with no drainage port in it.

If the field conditions are such that the drainage boundary is only at the bottom of the soil deposit and not above it, then the porous disc at the top shall be replaced by metal plate with no drainage port in it.

All these three type of tests shall be performed on the soil specimen extracted from the same Shelby tube, i.e. from the same soil strata. The test setup shown in FIG. 4 shall be used to determine three-dimensional coefficient of consolidation. These tests shall also allow to develop correlations to determine three-dimensional coefficient of consolidation when coefficient of consolidation in vertical direction using test setup shown in FIG. 2 and coefficient of consolidation in horizontal direction using test setup shown in FIG. 3 have been determined. Time rate of settlement both in vertical and horizontal directions and rate of volume change of a soil deposit can be accurately determined from the results available from these tests. Numerical analyses such as finite element analyses based on the results of these consolidation tests can then be made accurately to determine the volume change, rate of volume change with time, horizontal and vertical displacement, rates of horizontal and vertical displacements with time, and rate of increase in vertical and horizontal stresses with time, and rate of dissipation of excess pore-water pressures, in each and every single small soil element of soil element matrix.

(C) Installation Details for the Three-Dimensional Consolidation Test Device

The specimens from various depths of a cohesive deposit are obtained by use of Shelby tubes or other type of samplers. The sample shall be extracted from the samplers, in the same manner as is used to extract samples for one-dimensional consolidation test. For the three-dimensional consolidation tests using flexible ring, there is no need of shaping the specimen to push into fixed ring as is required for the one-dimensional consolidation test. After cutting to the required lengths and leveling the ends of the specimen, the specimen for three-dimensional consolidation test, shall be placed on the porous disc/base plate and then capped by top porous disc/loading head. Using a membrane expander, filter consisting of elastic filter fabric in the form a cylinder shall be installed around the soil specimen as is shown in FIG. 3 and FIG. 4. Using membrane expander, a thick rubber membrane shall be installed around the filter fabric/soil specimen as shown in FIG. 3 and FIG. 4. A thicker rubber membrane which can be installed using a membrane expander or other appropriate device, shall have some advantage over thinner membrane as a thick rubber membrane shall keep cylindrical shape along the joint space between the segment plates. It may be noted that filter fabric is not needed for test which allows dissipation of excess pore-water pressures in vertical direction only, as shown in FIG. 2.

Figure 5:
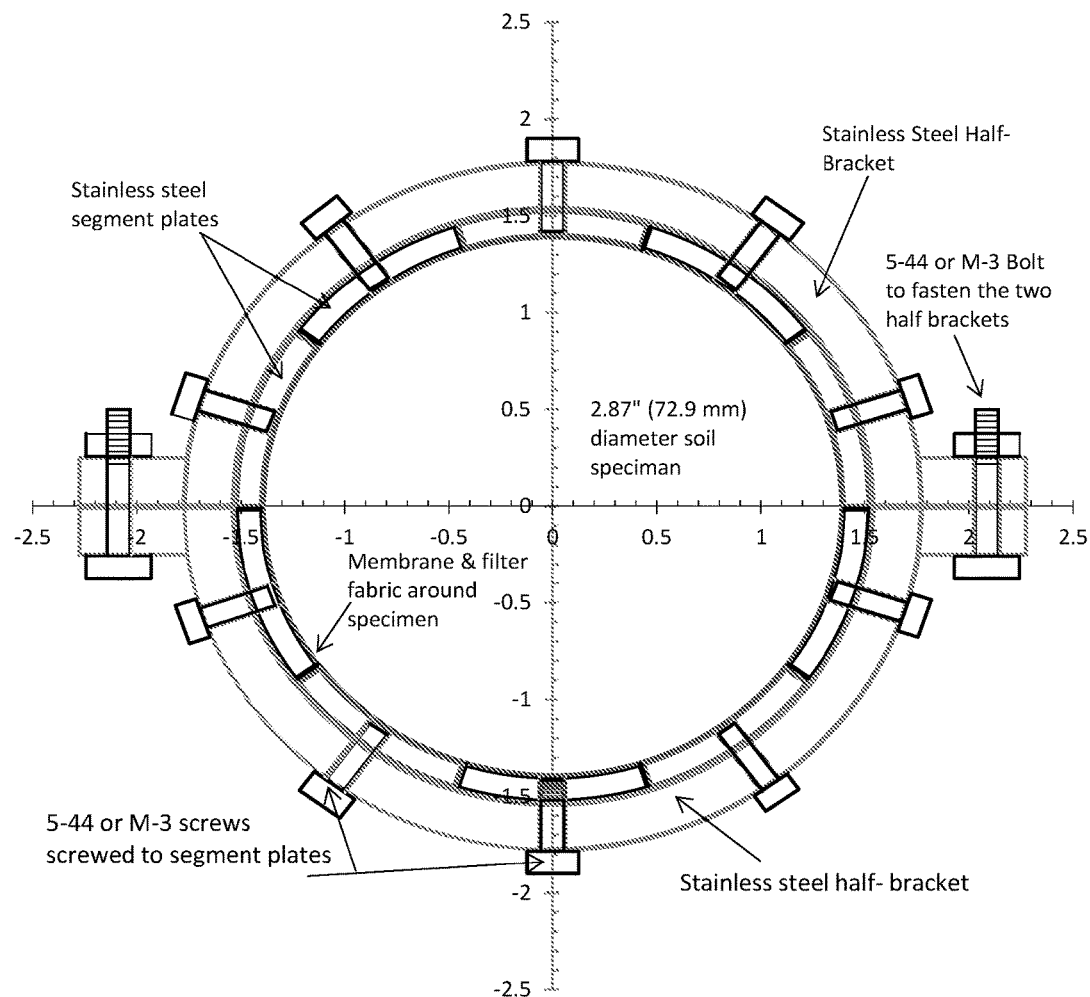
FIG. 5 shows schematic plan view detail of installing circular segment plates around the soil specimen using two half-circular brackets.
Figure 6:
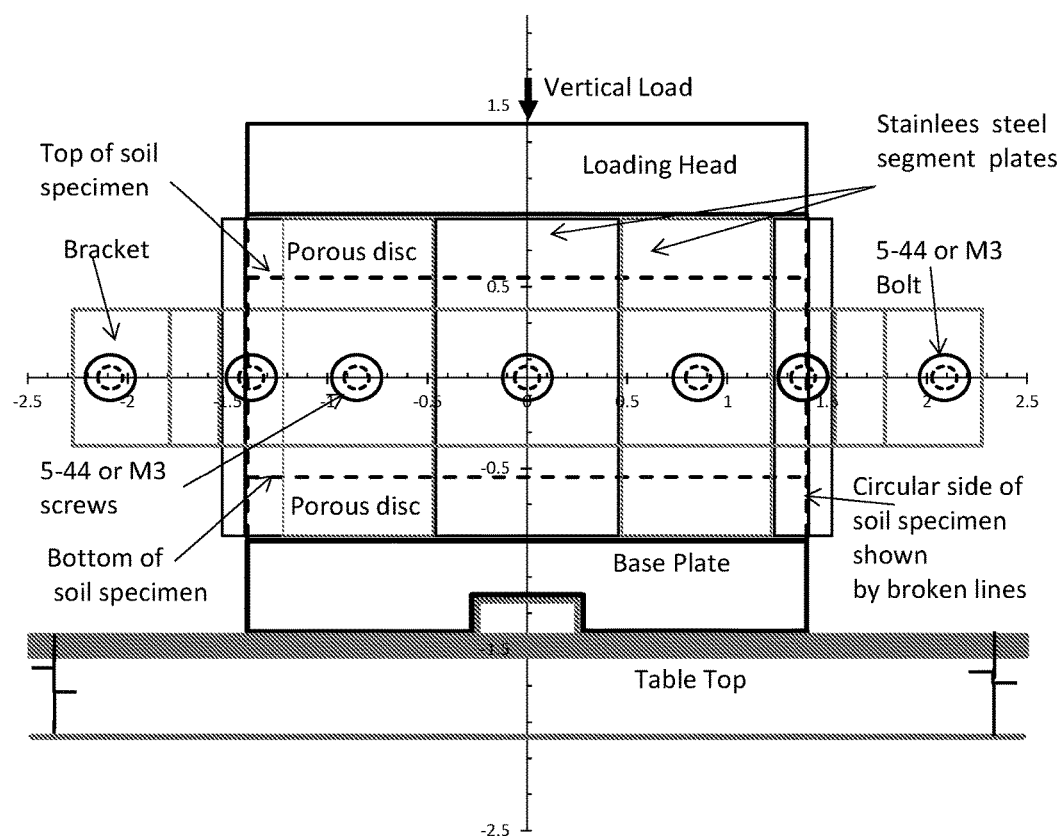
FIG. 6 shows schematic elevation view detail of installing circular segment plates around the soil specimen using two half-circular brackets.
Figure 7:
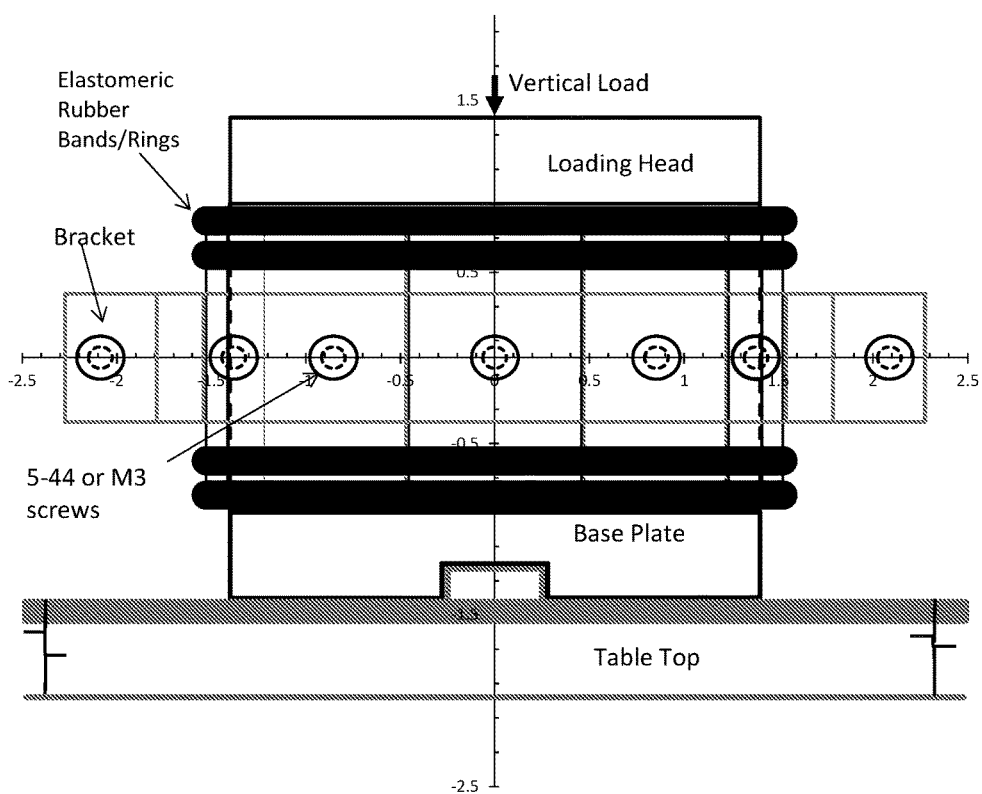
FIG. 7 shows the elevation view when elastomeric rubber bands have been slipped above and below the two half-circular brackets.
Figure 8:
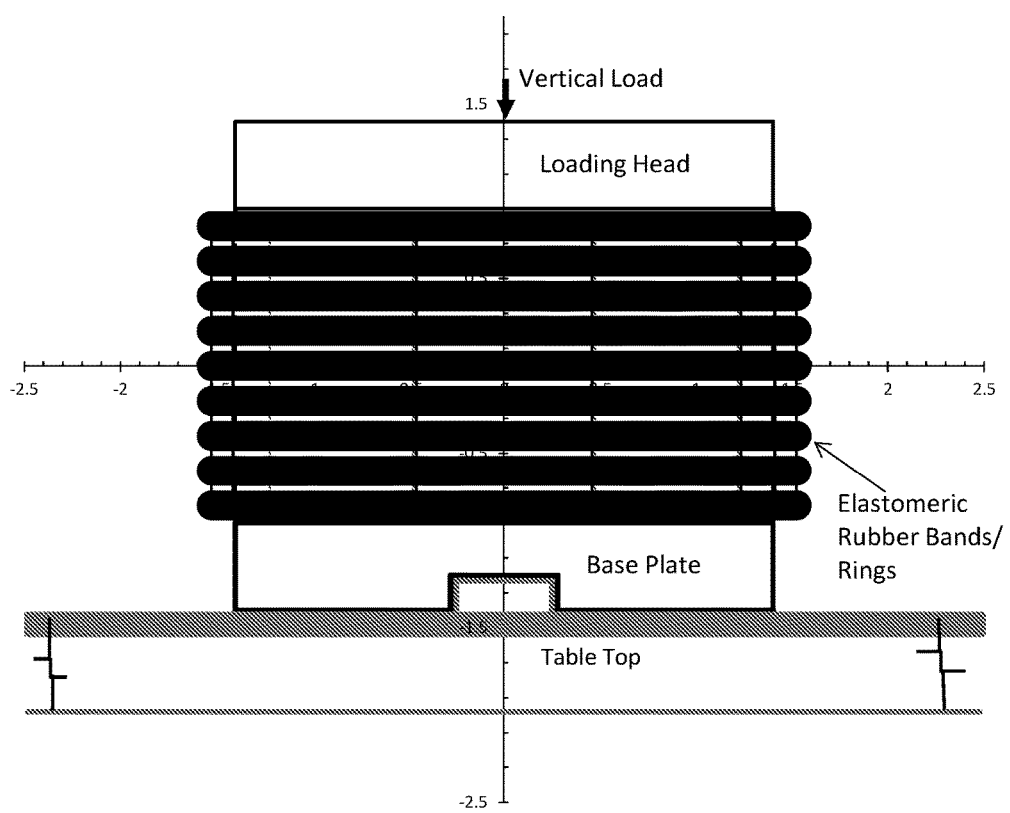
FIG. 8 shows the elevation view when both half-circular brackets have been un-installed and remaining rubber bands in the area previously occupied by brackets have been installed.

Commercially available woven or non-woven filter fabric can also be used after stitching it into a cylindrical shape using a strip of elastic cloth. Filter fabric can also be wrapped around the soil specimen with about ½" (12.7 mm) overlap and maintained stretched or taut in place by a 1" long adhesive tape at the ends. This tape shall be removed after installation of the rubber membrane around the specimen. Segment plates are installed around the membrane, using two half-circular brackets as shown in FIG. 5 and FIG. 6. The thickness of these brackets can vary between ¼" and ⅜" (6.35 mm and 9.53 mm). Elastomeric rubber bands of minimum ⅛" (3.2 mm) thickness are slipped on around the plates at marked locations as shown in FIG. 7. The width of rubber bands can vary between ⅛" and ½" (3.2 mm and 12.7 mm). The upper and lower brackets are then un-installed. Remaining rubber bands are slipped on around the plates in the space earlier covered by the bracket, as shown in FIG. 8. The expandable or flexible ring has thus been installed around the soil specimen. Since segmental circular plates are resting against the top and bottom porous discs or base plate and loading head, initially the lateral load exerted by rubber bands acts on the porous discs and very little, if any, directly on the soil specimen in the beginning of the test. When specimen begins to undergo lateral displacement or lateral expansion during the test, the rubber bands around the segmental plates shall stretch and exert pressure on the segmental plates thereby on the surface of the soil specimen all along its height and shall help in maintaining the uniform diameter through its height during the test; the plates are then not in contact with porous discs and so rubber bands exerts lateral pressure on the specimen. As many rubber bands as needed to maintain uniform diameter of cylindrical specimen and also to resist lateral pressures proportional to the applied vertical load during the test, shall be used. The inside surface of segment plates shall be lubricated to reduce friction between rubber membrane around soil specimen and the plates. The function of segmental stainless steel plates is to uniformly distribute the lateral load applied by rubber bands on the soil specimen.

Figure 9:
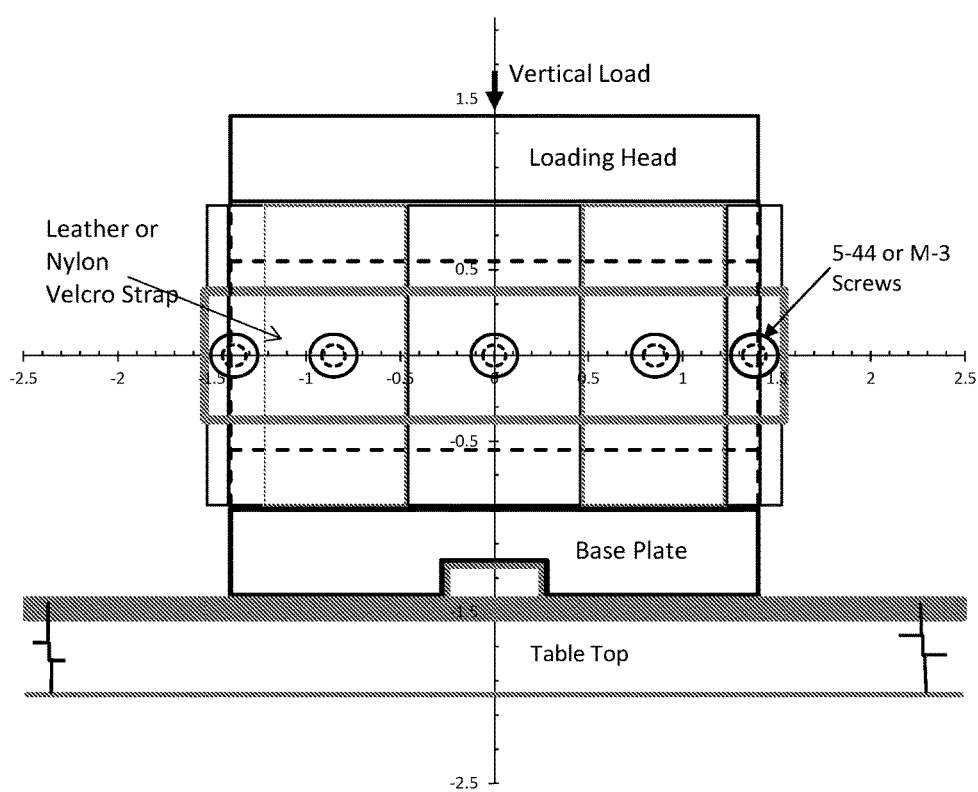
FIG. 9 shows the installation of circular segment plates using leather or nylon Velcro straps, instead of using two half-circular brackets.
Figure 10:
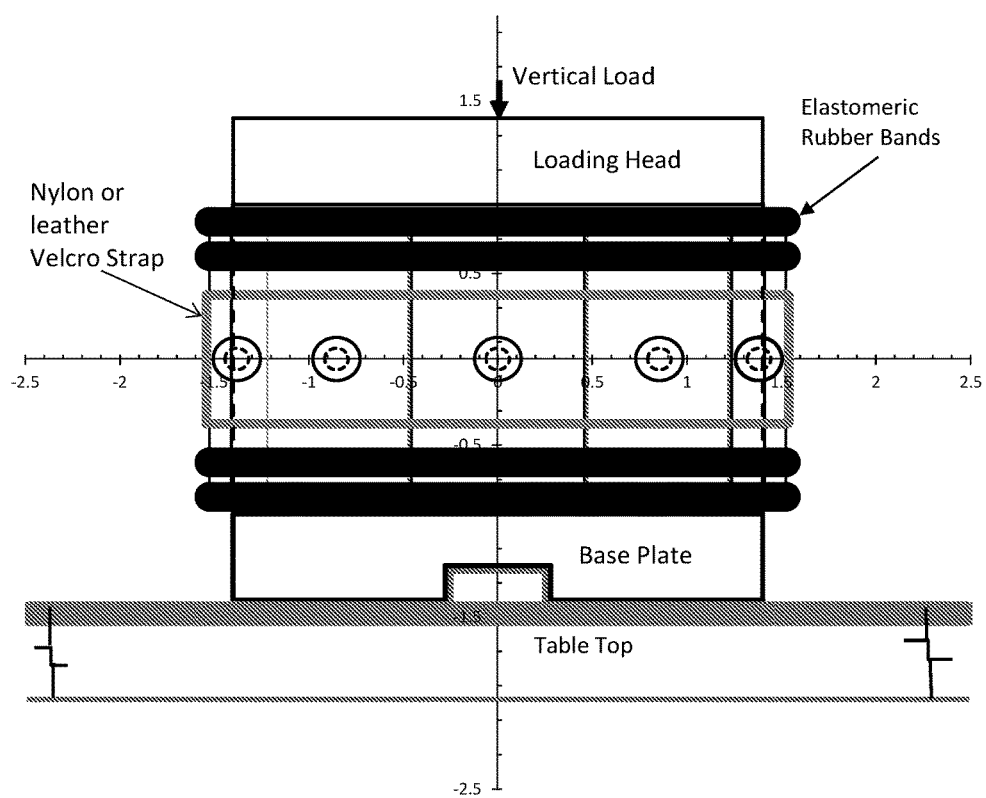
FIG. 10 shows the elevation view when elastomeric rubber bands have been slipped above and below and above the Velcro straps.
Figure 11:
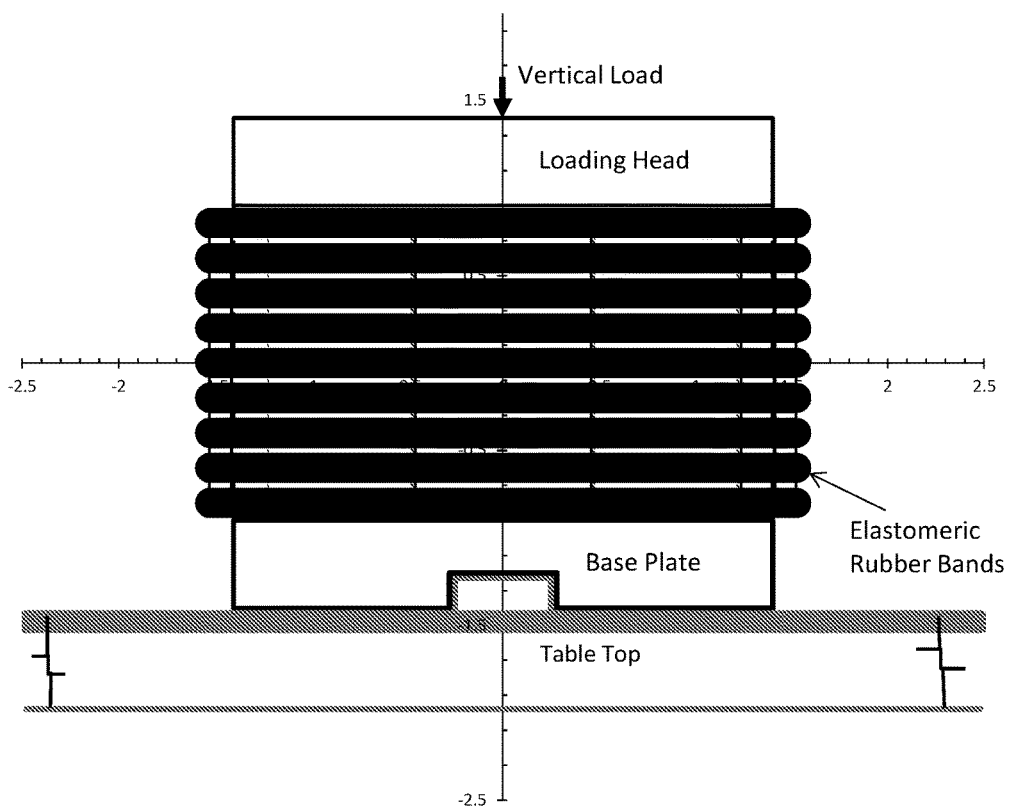
FIG. 11 shows the elevation view when Velcro strap has been un-installed and remaining rubber bands in the area previously occupied by brackets have been installed. Thus installation of flexible ring using Velcro straps has been completed.
Figure 12:
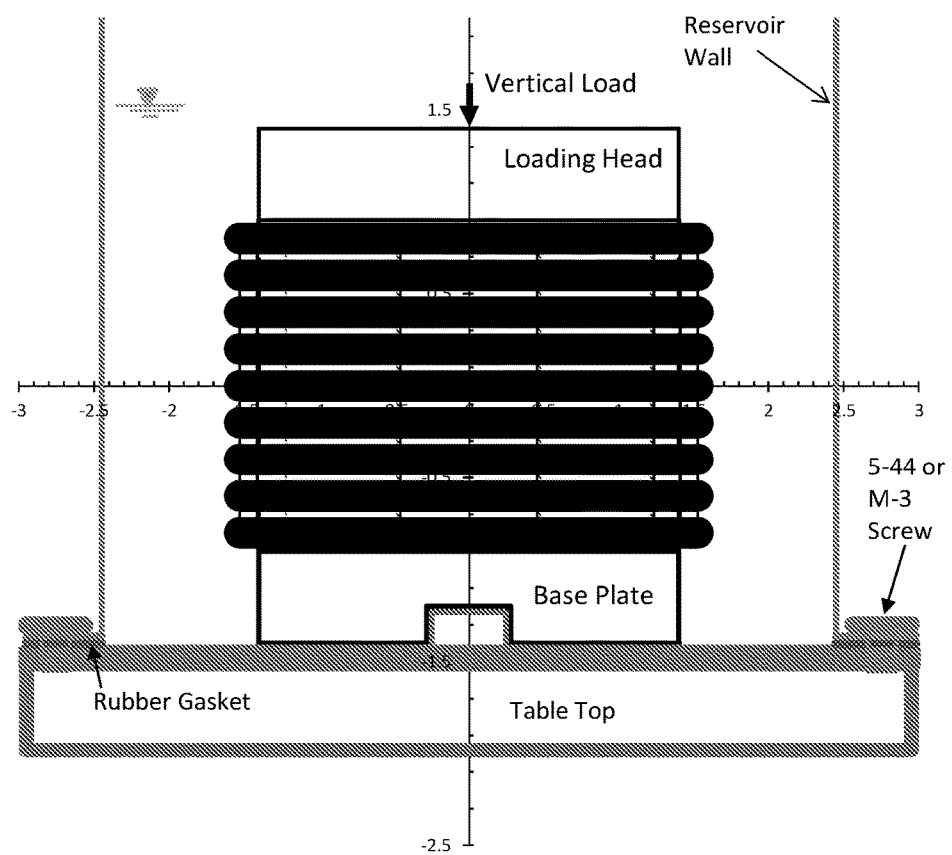
FIG. 12 shows an elevation view of installation of the reservoir cylindrical wall made of stainless steel or of Perspex. At the base the Wall is clamped to the table top using a rubber gasket for water tightness and 5-44 or M-3 screws.

Alternatively, the lubricated segment plates can be assembled around soil specimen by use of a 1" (25.4 mm) wide leather or nylon or polyester or polypropylene Velcro straps. First, segment plates are fastened to Velcro strap using 5-44 or M-3 screws as shown in FIG. 9 (other screw sizes may be used along with appropriate female threads in segment plates). Then the assembled plates are wrapped around the soil specimen and maintained in position by Velcro strap as shown in FIG. 10. The rubber bands of minimum thickness of ⅛" (3.17 mm) are slipped on around the plates as shown in FIG. 11. The screws are unthreaded to remove the straps. The remaining rubber bands are then slipped on around the plates in the space earlier occupied by the Velcro straps, as shown in FIG. 12. The expandable jacket has now been installed around the soil specimen.

Sizes of segment plates, half brackets and rubber bands shown in FIG. 2 through FIG. 9 and described in the text above are based on soil specimen diameter of 2.87" (72.9 mm) in diameter. Diameter of soil specimen is also dependent on inside diameter of Shelby tubes or other type of samplers used for extracting the samples from a cohesive deposit. Inside diameter of Shelby tubes as per ASTM standards are 1.905" (48.42 mm), 2.87" (72.9 mm) and 4.76"

(120.9 mm). The diameter of circular arch shaped segment plates and two half brackets shall depend on the diameter soil specimen. Number of segment plates shall be 8, 10 and 16 for soil specimen of 1.905" (48.42 mm), 2.87" (72.9 mm) and 4.76" (120.9 mm), respectively. For other specimen sizes, special design detail shall be used.

(d) Cross-Sectional Area at a Given Load

Rubber membrane is used to encase the specimen to provide reliable protection against leakage and also for separation between soil specimen and the reservoir/chamber fluid. The membrane is sealed to the specimen cap and base with rubber O-rings. The flexible ring encasing the soil specimen maintains uniform diameter through its height. Area of cross section, A, for a given applied load at an instant of time t, is approximately given by:

$$A = \frac{A_c}{(1 - \varepsilon_v)} \quad (1)$$

Where:
$A_c$=Average cross-sectional area of the specimen after consolidation and before beginning the test.
$\varepsilon_v$=Axial strain for the given axial load at any instant time t=$\Delta H/H$
$\Delta H$=Change in height of specimen during loading
H=height of specimen after consolidation.
D=Diameter of specimen after consolidation.

Each increment of load is maintained for 24 hours and drainage is allowed during the test. Therefore, pore-water pressures which develop instantaneously after application of the load, are allowed to dissipate almost to a zero value. Thus at each increment of load, the settlements in the soil specimen continues to occur from beginning of the application of increment for all the 24 hours. Eq. 1 does not take into account the settlement which occurs at each increment of load. For the three-dimensional consolidation test, the lateral displacement of the specimen during the test shall also be measured by two linear variable differential transformers (LVDTs) placed diametrically opposite to each other to measure radial displacement and the above equation shall be corrected when enough data is available. In the drawings, LVDTs and their mounting system has not been shown. Volume of specimen shall be calculated based on measured height and measured diameter. Area of specimen shall be calculated based on measured diameter.

(e) Lateral Resistance Provided by Rubber Bands, Membrane and Elastic Filter Fabric During the test, when an additional vertical load increment is applied, the lateral stress increases which thereby is resisted by the elastomeric rubber bands, rubber membrane and filter fabric. These elastic elements stretch/expand during the test; the magnitude of expansion or increase in diameter is proportional to the lateral load and their modulus of elasticity. The increase in lateral stress for each increment of load shall be equal to vertical stress times Poisson's ratio. The magnitude of the lateral stress cannot be allowed to exceed the tensile strength of these elastic elements. The magnitude of lateral stress is proportional to vertical stress applied during the test. Therefore vertical load to be applied during the test has to be limited so that the tensile strength of these elements is not exceeded. For this purpose the vertical load shall not be increased any further, when the rate of increase in diameter as measured by LVDTs increases suddenly, indicating that the failure is approaching.

Figure 13:
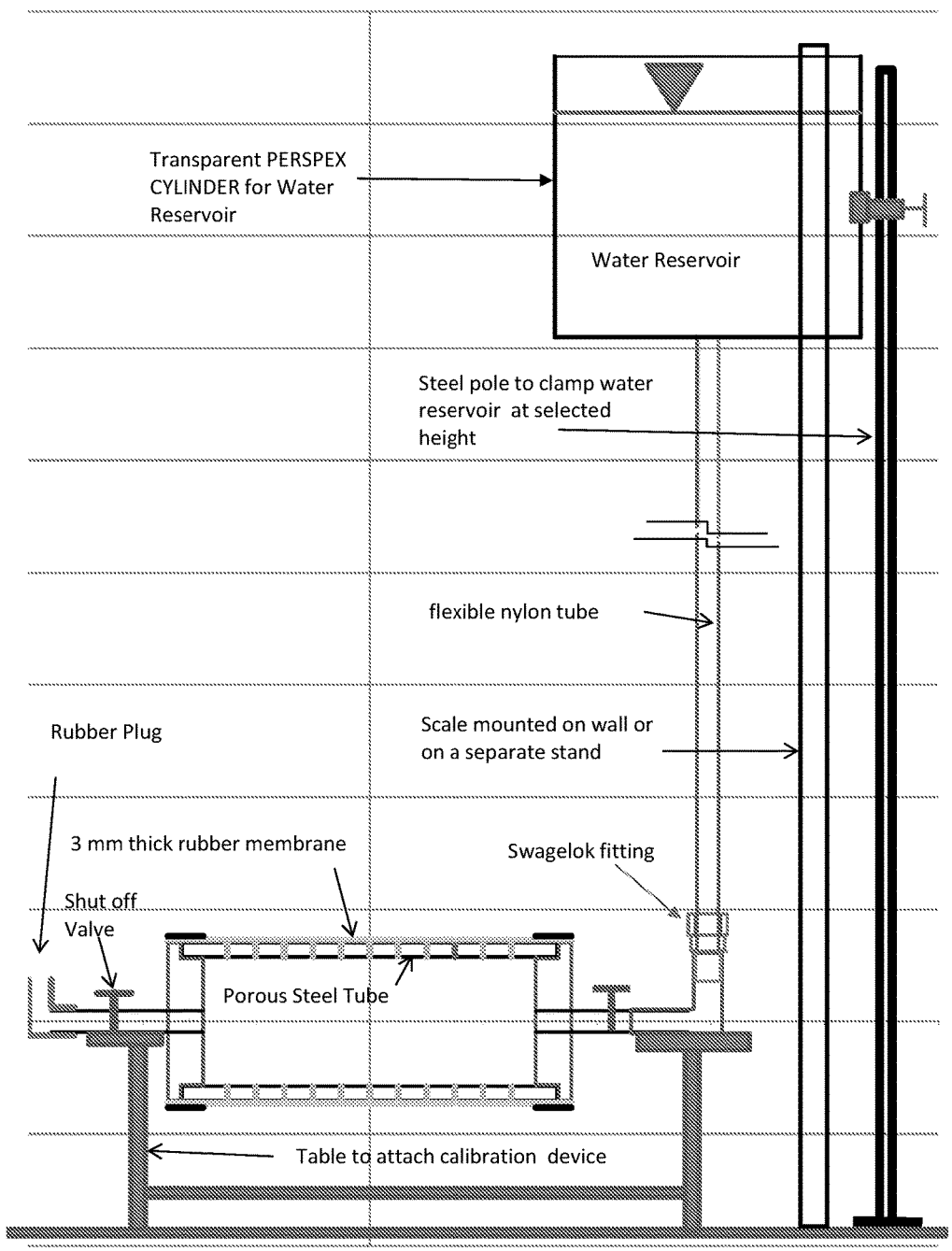
FIG. 13 shows the calibration device.
Figure 14:
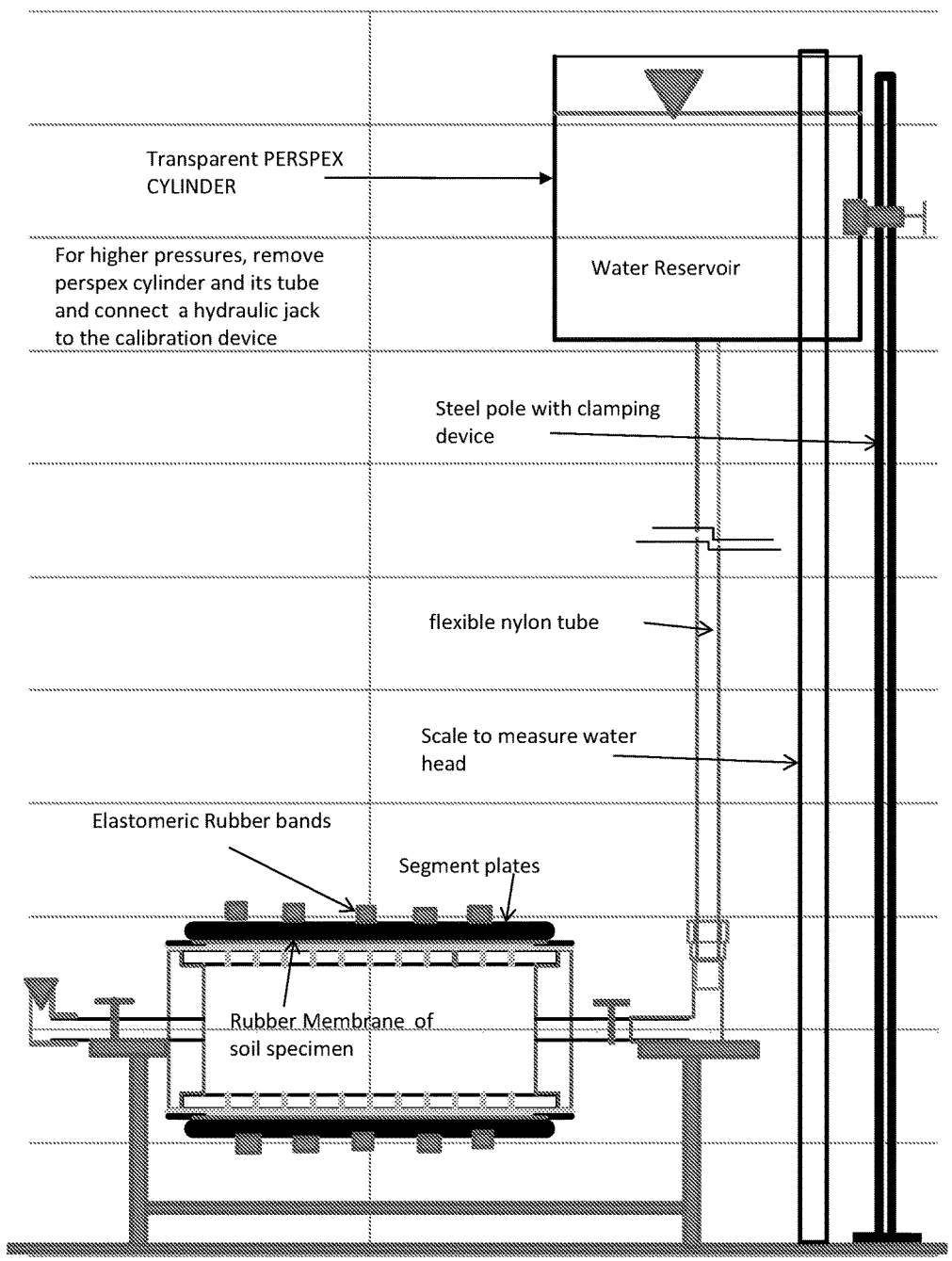
In FIG. 14, the flexible ring has been mounted around the calibration device for performing calibration of flexible ring to determine the hydraulic pressure versus lateral strain relationship and thereby to determine combined modulus of elasticity of filter fabric, rubber membrane and elastomeric rubber membrane.

A calibration device as shown in FIG. 13 and FIG. 14 shall be used to provide the data for the magnitude of lateral stress versus the increase in diameter (or lateral strain) of rubber membrane/elastomeric rubber bands/filter fabric. This data shall help in calculating the combined modulus of elasticity of these elastic elements installed around the specimen. To measure increase in diameter of these elastic elements during calibration, LVDTs shall be installed around the segment plates/rubber bands. In the drawings, the LVDTs and their mounting system has not been shown.

The Perspex cylindrical reservoir, 4" to 12" (100 and 300 mm) in diameter, shall be raised by a foot (0.3 m) each time to expand the calibration device as shown in FIG. 13 and also on flexible ring mounted on calibration device as shown in FIG. 14 to provide data of expansion of these elastic elements with increase in water head or hydraulic pressure. The reservoir can be raised to any height varying between 2 and 8 ft (0.6 and 2.4 m) or to greater height depending on the headroom of the laboratory. If higher pressures are needed for calibration, the water reservoir shall be disconnected and a hydraulic pump of a very low capacity (maximum of 40 psi) shall be connected to the calibration device to perform the calibration up to 20 psi pressure. The pressure shall be increased in increments of 0.5 to 1 psi.

The calibration device consists of a porous stainless steel tube with end caps sealed for water tightness. 3 to 5 mil thick rubber membrane is mounted on porous stainless steel tube. The rubber membrane is clamped at the ends of porous stainless steel tube for water tightness. On one end, a brass tube shall outlet the porous stainless steel tube to remove the air bubbles from water when hydraulic fluid is filled in the porous steel tube. When air bubbles are not seen coming out from the tube, the valve shall be closed. The brass tube on the other end of the porous stainless steel tube shall lead towards the reservoir or for higher pressure calibration to the hydraulic pump.

The calibration of the calibration device as shown in FIG. 13 shall be first done and data recorded in Table 1. Thereafter, the rubber membrane, (same as to be used during the test around the soil specimen), filter fabric, segment plates and rubber bands shall be mounted on 3 to 5 mil (mm) thick rubber membrane. These elements shall be mounted on the rubber membrane with the help of half-brackets or Velcro straps as previously detailed in FIG. 2 through FIG. 9. The calibration of the calibration device shall be done raising pump pressure each time by 0.5 psi. The calibration data shall be recorded in Table 2. The lateral stress exerted by 3 to 5 ml thick rubber membrane shall be deducted from the lateral stress exerted by 3 to mm thick rubber membrane of calibration device plus the 3 to 5 ml thick rubber membrane, filter fabric and rubber bands for determining the value of lateral stress being exerted on the flexible ring consisting of rubber membrane, filter fabric and rubber bands at various levels of lateral strain, when vertical load is applied during the test. The calibration data shall also be used to calculate the combined modulus of elasticity of these elastic elements. For test method shown in FIG. 2, calibration shall be done on flexible ring consisting of the rubber membrane, segment plates and rubber bands. Lateral strain shall be calculated from the value of radial displacement measured by two LVDTs, placed diametrically opposite to each other. The product of lateral strain with combined modulus of elasticity shall provide the value of lateral stress at any instant of time during application of vertical load during the test.

Since, there is a limit for the vertical load which can be applied during the test, as explained above, this limit shall depend on the tensile strength of the elastomeric rubber bands. For higher vertical load, the elastomeric rubber bands shall be replaced by a jacket consisting of stainless steel springs, which can stretch and also resist vertical loads up to 32 tons per sq. ft (tsf). In this case, calibration shall be done for the spring jacket in place of elastomeric rubber bands.

Even triaxial compression tests do not provide accurate estimate of horizontal and vertical settlements and modulus of elasticity because lateral stresses do not increase but remain equal to applied chamber pressure though out the test, i.e. the lateral stresses do not increase as is estimated by theory of elasticity.

(f) Loading Device for Vertical Load

Incremental consolidation load frame/test system shall be the same as described in ASTM D-2435 and AASHTO T-216. The test shall be performed at vertical load increments of ½, 1, 2, 4, 8, 16 and 32 tsf. Each load increment shall be maintained for 24 hours and readings taken at intervals described in ASTM D-2435. The test device as shown in FIG. 2, FIG. 3 and FIG. 4 are adaptable to these loading devices.

Triaxial compression test setups consisting of triaxial chamber, chamber pressure and control panel can also be used for performing 3-D consolidation tests. But the loading system of triaxial test setup shall not be used. Instead incremental load frame/test system shall be suitably modified to fit on the chamber system to apply vertical load increments to maintain each load increment for 24 hours. The height of chamber shall be about half or less than half of the height of the triaxial chamber, because the height of specimen for consolidation tests shall be between 1" (25.4 mm) or about half to three-quarter of the height of the diameter of the soil specimen. Soil specimen for triaxial compression test, is generally about two times the diameter.

There are some important advantages of using a chamber system along with incremental consolidation load frame. In the chamber filled with water, fluid pressure can be applied equivalent to insitu horizontal earth pressure calculated for the depth from where the soil specimen was extracted for performing the consolidation test. Incremental loading system then shall predict both vertical and horizontal settlements of the soil at various values of loads at that particular depth. If there is thick soil deposit, and soil specimen have been extracted from various depths, a detailed data of horizontal and vertical settlements at various load increments shall be available at various depths of the same soil deposit. This will also help in providing data of insitu modulus of elasticity of soil at various depths.

In general, the stresses computed from the theory of elasticity are function of Poisson's ratio. However, vertical stresses resulting from normal stresses applied to the surface are always independent of Poisson's ratio. Vertical and horizontal stresses caused by strip load are also independent of Poisson' ratio (Lambe and Whitman, 1969). Horizontal stresses caused under a circular area depend on Poisson's ratio. Therefore, in three-dimensional consolidation tests, it is important that horizontal stresses caused by vertical stress on top of the specimen be approximately equal to those predicted by theory of elasticity either for strip load or for circular load. In three dimensional consolidation test, as vertical load is increased, the horizontal resistance on the sample increases as a product of lateral strain in rubber bands/membrane/filter fabric and its modulus of elasticity. Lateral strain during the test is calculated from measurements by LVDT. Combined modulus of elasticity of rubber bands, rubber membrane and elastic filter fabric is measured by the calibration device at various values of lateral strain. Therefore, ideally or theoretically, the combined modulus of elasticity of rubber bands, rubber membrane and elastic filter fabric during 3-D consolidation test should develop an increase in lateral resistance which should be equal to the increase estimated to occur in soil by the theory of elasticity at the same increment of the vertical load The various types of elastomeric rubber bands are manufactured and the modulus of elasticity of these types can very between 100 to 800 psi (689 to 5516 kPa). The lateral resistance shall also depend on the thickness, width and number of elastomeric rubber bands. Therefore, for three-dimensional consolidation tests, it shall be advisable to select the sizes and number of elastomeric rubber bands and their modulus of elasticity with the consideration that the increase in lateral resistance during the 3-D consolidation test is approximately the same as the increases in horizontal stresses in soil predicted by theory of elasticity.

(g) Conclusions

With the invention of test device for determining three-dimensional consolidation properties of soils using a flexible ring in place of a rigid ring of the one-dimensional consolidation test, as detailed above, it shall be possible to determine the following for both for normally and overconsolidated soils: (i) Horizontal and vertical settlements, (ii) Coefficient of consolidation in vertical direction ($c_v$) when both horizontal and vertical settlements are taking place like those which occur insitu at various depths when vertical loads are applied, (iii) Coefficient of consolidation in horizontal direction ($c_h$) when both horizontal and vertical settlements are taking place like those which occur insitu at various depths when vertical loads are applied, (iv) Three-dimensional coefficient of consolidation, $c_{3-D}$, (i.e. resultant of $c_v$ and $c_h$), when both horizontal and vertical settlements are taking place like those which occur insitu at various depths when vertical loads are applied, (v) Correlations between $c_v$ with depth and with vertical and horizontal stresses, (vi) Correlations between $c_h$ with depth and with vertical and horizontal stresses, (vii) Correlations between ratio $c_h/c_v$ with depth and also with increase in vertical and horizontal stresses, (viii) Modulus of elasticity in vertical direction (E) at various depths and vertical loads, (ix) Correlations between $E_v$ with depth and with vertical and horizontal stresses, (xii) Correlations of $c_{v1}$, $c_h$, and $E_v$ with density of soils, and (xiii) Although laboratory soil tests such as one-dimensional consolidation test and triaxial compression tests are being conducted for last more than 100 years, these values as described above have not been determined accurately in laboratory, but with the invention of test device for determining three-dimensional consolidation properties allowing both vertical and horizontal settlements, it will be possible to determine these values correctly because field conditions shall be simulated in the geotechnical testing laboratories.

TABLE 1

Form for entering data to calibrate the calibration device

| Serial No. | Water Head in ft. or m or Water Pressure in psi or kPa above Centerline of Porous Stainless steel Tube | Increase in Diameter of membrane, Δd (inch or mm) as measured by LVDWT or calculated from head measured in reservoir | Lateral Strain, $\varepsilon_l = \Delta d/d$ | Water Pressure ($p_w$) in psi (kg/mm$^2$) | Modulus of Elasticity (E) of rubber In psi or kg/mm$^2$ |
|---|---|---|---|---|---|
| | | ... | ... | ... | ... |
| | | | | | |
| | | | | | |
| | | | | | |
| | | | | | |
| | | | | | |
| | | | | | |
| | | | | | |
| | | | | | |
| | | | | | |

Outside diameter of porous stainless tube with 3 mil thick rubber membrane, d = . . . ,
Length of 3 mil thick rubber membrane between end clamps, L = . . .
Cross-sectional Area of device, A = π d$^2$/4, Volume of device = A * L
Inside diameter of reservoir = $d_r$, Cross-sectional Area of reservoir, $A_r$ = π $d_r^2$/4
Increase in Diameter of device, Δd, as measured by LVDWT
E of rubber membrane = $p_w/\varepsilon_l$

TABLE 2

Form for entering data to calibrate the flexible ring

| Serial No. | Water Head in ft. or m or Water pressure in psi or kPa above the Centerline of Porous Stainless steel Tube | Increase in Diameter of rubber bands, Δd (inch or mm) | Lateral Strain, $\varepsilon_{rb} = \Delta d/d_p$ | Water Pressure ($p_w$) in psi or kPa | Combined Modulus of Elasticity (E) of rubber bands, filter fabric & rubber membrane in psi or kPa |
|---|---|---|---|---|---|
| | | ... | ... | ... | ... |
| | | | | | |
| | | | | | |
| | | | | | |
| | | | | | |
| | | | | | |
| | | | | | |
| | | | | | |
| | | | | | |
| | | | | | |

Outside diameter of rubber bands before beginning calibration, d = . . . ,
Length of rubber membrane between end clamps, L = . . .
Increase in Diameter of rubber bands, Δd = . . .
Outside diameter of segmental plates before beginning of test = $d_p$
Outside diameter of filter fabric = $d_f$
Outside diameter of rubber membrane = $d_m$
Lateral strain of rubber bands, $\varepsilon_{rb} = \Delta d/d$

REFERENCES

ASTM Standards (2011), Standard Test Method for Determining One-Dimensional Consolidation Properties of Soils, ASTM D2435/D2435 M-11, American Society of Materials, Philadelphia, Pa.

AASHTO (2012), Standard Method of Test for One-Dimensional Consolidation Properties of Soils, American Association of State Highway and Transportation Officials, Washington, D.C.

Fang, H (1990), Foundation Engineering Handbook, $2^{nd}$ Edition, Van Nostrand Reinhold, New York.

HRB (1973), Estimating Consolidation Settlements of Shallow Foundations on Overconsolidated Clay, Application Bulletin prepared by Committee A2L02, Properties of Soli and Rock, Highway Research Board, Washington, D.C.

Perloff, W. H., and Baron, W. (1976), SOIL MECHANICS, John Wiley and Sons, New York.

Skempton, A. W., and Bjerrum, L. (1957), A Contribution to the Settlement Analyses of Foundations on Clay, Geotechnique 7, No. 3

Terzaghy, K, Peck, B. P., Mesri, G. (1996), Soil Mechanics in Engineering Practice, Wiley-Interscience, New Yor Winterkorn H. F., and Fang, H. (1975), Foundation Engineering Handbook, Van Nostrand Reinhold Company, New York.

The invention claimed is:

1. The test system to determine three-dimensional consolidation properties of soils, the test system comprising:
   a. A test device comprising:
      (i) an incremental loading system or a triaxial loading system;
      (ii) a triaxial type control panel;
      (iii) a chamber comprising metal or acrylic vertical walls, a top plate, and a base plate; wherein the metal or acrylic vertical walls are held in place by the top plate and the base plate by clamping rods between the top plate and the base plate;
      (iv) a first porous disc resting on the base plate to receive a soil specimen within a chamber or an open reservoir;
      (v) a second porous disc, placed on top of the soil specimen;
      (vi) a loading head placed on top of the second porous disk;
      (vii) a filter fabric placed such that the filter fabric surrounds and is in contact with the soil specimen;
      (viii) a rubber membrane placed such that the rubber membrane surrounds and is in contact with the filter fabric;
      (ix) a plurality of segmented circular shaped stainless steel plates assembled vertically such that the assembled segmented plates surround and are in contact with the rubber membrane, and wherein each of the segmented stainless plates contains at least one screw mount for the removable attachment of two horizontal separate half-circular brackets, a horizontal nylon hook and loop strap, or a horizontal leather hook and loop strap for vertical and horizontal positioning of each of the segmented stainless steel plates; wherein the screw mounts are located at the mid-height of each of the segmented stainless steel plates; wherein each of the segmented stainless steel plates extend vertically beyond the first and second porous disc;
      (x) at least one elastomeric rubber band placed such that each of the at least one elastomeric rubber band surround and are in contact with each of the segmented stainless steel plates;
      (xi) at least one LVDT or strain gage for measuring the value of radial displacement removably attached to the at least one elastomeric rubber band;
   b. and a calibration device for determining a combined modulus of elasticity of the filter fabric, the rubber membrane, the segmented stainless steel plates, and the at least one elastomeric rubber band or ring, the calibration device comprising:
      (xii) a vertically movable water reservoir;
      (xiii) a horizontal porous stainless steel tube connected to the vertically movable water reservoir via at least one tube, wherein the porous stainless steel tube is configured to be surrounded and sealed by an additional rubber membrane and wherein the additional rubber membrane is configured to be surrounded by a combination of the filter fabric, the rubber membrane, the segmented stainless steel plates, and the at least one elastomeric rubber band.

2. The test system to determine three-dimensional consolidation properties of soils, the test system comprising:
   a. A test device comprising:
      (i) an incremental loading system or a triaxial loading system;
      (ii) an open metal reservoir comprising a metal cylindrical vertical wall and metal circular base plate, wherein metal wall and base plate held in place by screws;
      (iii) a first porous disc resting on the base plate to receive a soil specimen within the a chamber or an open reservoir;
      (iv) a second porous disc, placed on top of the soil specimen;
      (v) a loading head placed on top of the second porous disk;
      (vi) a filter fabric placed such that the filter fabric surrounds and is in contact with the soil specimen;
      (vii) a rubber membrane placed such that the rubber membrane surrounds and is in contact with the filter fabric;
      (viii) a plurality of segmented circular shaped stainless steel plates assembled vertically such that the assembled segmented plates surround and are in contact with the rubber membrane, and wherein each of the segmented stainless plates contains at least one screw mount for the removable attachment of two horizontal separate half-circular brackets, a horizontal nylon hook and loop strap, or a horizontal leather hook and loop strap for vertical and horizontal positioning of each of the segmented stainless steel plates; wherein the screw mounts are located at the mid-height of each of the segmented stainless steel plates; wherein each of the segmented stainless steel plates extend vertically beyond the first and second porous disc;
      (ix) at least one elastomeric rubber band placed such that each of the at least one elastomeric rubber band surround and are in contact with each of the segmented stainless steel plates;
      (x) at least one LVDT or strain gage for measuring the value of radial displacement removably attached to the at least one elastomeric rubber band;
   b. and a calibration device for determining a combined modulus of elasticity of the filter fabric, the rubber membrane, the segmented stainless steel plates, and the at least one elastomeric rubber band or ring, the calibration device comprising:

(xi) a vertically movable water reservoir;

(xii) a horizontal porous stainless steel tube connected to the vertically movable water reservoir via at least one tube, wherein the porous stainless steel tube is configured to be surrounded and sealed by an additional rubber membrane and wherein the additional rubber membrane is configured to be surrounded by a combination of the filter fabric, the rubber membrane, the segmented stainless steel plates, and the at least one elastomeric rubber band.

* * * * *